United States Patent [19]

Frances et al.

[11] Patent Number: 4,970,115
[45] Date of Patent: Nov. 13, 1990

[54] CURABLE POLYORGANOSILOXANE COMPOSITIONS COMPRISING LATENT TIN CATALYSTS

[75] Inventors: Jean-Marc Frances, Villeurbanne; Veronique Gouron, Talence; Bernard Jousseaume, Talence; Michel Pereyre, Talence, all of France

[73] Assignee: Rhone-Poulenc Chimie, Courbevoie, France

[21] Appl. No.: 341,765

[22] Filed: Apr. 21, 1989

[30] Foreign Application Priority Data

Apr. 21, 1988 [FR] France ................... 88 05555

[51] Int. Cl.$^5$ ............................................. B32B 33/00
[52] U.S. Cl. ........................................ 428/332; 428/447;
528/18; 524/588; 524/861; 524/464; 524/379;
524/386; 524/792; 524/765
[58] Field of Search ................. 528/18; 524/588, 861,
524/464, 379, 386, 792, 765; 428/447, 332

[56] References Cited

U.S. PATENT DOCUMENTS 4,719,243 1/1988 Pocknell ........................... 528/31
4,734,479 3/1988 Masatoshi et al. ................ 528/18
4,830,925 5/1989 Swihart et al. ................... 528/18

*Primary Examiner*—Melvyn I. Marquis
*Attorney, Agent, or Firm*—Burns, Doane Swecker & Mathis

[57] ABSTRACT

Storage-stable, curable polyorganosiloxane compositions, whether solvent-free, in solution in an organic solvent or in aqueous emulsion, contain (A) a polydiorganosiloxane having silanol endgroups, (B) a polydiorganohydrosilane, and (C) a catalytically effective amount of a latent tin catalyst of the formula (1):

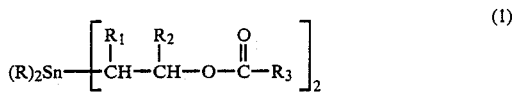

and are cured into elastomeric state by heating to a temperature at least equal to the decomposition temperature of the latent catalyst (C); such polyorganosioxane compositions are well adopted for the thin-layer coating of a wide variety of useful substrates, e.g., paper.

9 Claims, No Drawings

CURABLE POLYORGANOSILOXANE COMPOSITIONS COMPRISING LATENT TIN CATALYSTS

CROSS-REFERENCE TO COMPANION APPLICATION

Our copending application, Ser. No. 341,633, filed concurrently herewith and assigned to the assignee hereof.

BACKGROUND OF THE INVENTION

1. Field of the Invention:

The present invention relates to novel organopolysiloxane compositions containing a "latent" tin catalyst that are capable of being crosslinked into elastomeric state, for example, in thin layer form.

2. Description of the Prior Art:

Curable organopolysiloxane compositions are well known to this art that crosslink in the presence of a tin or platinum (C) catalyst by a polycondensation reaction between a polydiorganosiloxane (A) having silanol end groups and a polydiorganosiloxane (B) containing at least three SiH (silicon hydride) groups per molecule.

These compositions, generally free from inorganic fillers, can be used for producing a non-adhesive and/or water-repellent elastomeric coating on various substrates (supports), in particular on paper and on films made of a plastic material, such as polyolefin, polyester, regenerated cellulose, or even metal or the like, with a view to depositing a silicone coating (thin layer), the thickness of which can range from approximately 1 μm to a few mm.

The known industrial compositions can be divided into three basic groups:

(i) solvent-free compositions in which the polymers (A) and (B) are employed in bulk, namely, substantially without any organic solvent. Compositions of this type are described, in particular, in British Patents Nos. GB-A-1,374,792 and GB-A-1,504,716, where the catalyst (C) is a platinum compound. The mixture of the polymers (A) and (B) must then exhibit a viscosity of less than approximately 5000 mPa.s at 25° C.;

(ii) the compositions in solution in an organic solvent, in which the polymers (A) and (B) may exhibit very high viscosities, which can improve the quality of the coating. The solvent is then removed by heating during the crosslinking. Such compositions containing a tin catalyst (C) are described, for example, in patents U.S. Pat. No. 3,061,567 and No. GB-A-1,504,716;

(iii) the aqueous emulsion compositions containing water and an emulsifying agent in addition to the three constituents (A), (B) and (C). The water is removed by heating during the crosslinking. Compositions of this type are described, for example, in U.S. Pat. Nos. 4,127,460, 4,288,356 and 4,624,900.

All of the known compositions of the aforementioned types exhibit the characteristic of being insufficiently stable over long-term storage. This is the reason the commercial forms thereof all exist as at least two components (or two packs) which the user mixes when required. After mixing, the composition has a pot life which typically is not longer than 48 hours.

It is quite apparent that such packaging in at least two packs constitutes a serious constraint both for the manufacturer and, above all, for the user of the composition.

Indeed, in conducting the mixing, the user, in particular, can make a mistake in measuring out and/or preparing too much mixture for his actual needs, resulting in a loss of product, which gels and therefore becomes unusable once the pot-life period has expired.

SUMMARY OF THE INVENTION

Accordingly, a major object of the present invention is the provision of improvedly storage-stable, curable organopolysiloxane compositions which comprise a latent tin catalyst which is inactive at ambient temperature, but which becomes active when the temperature is increased.

Another object of the present invention is the provision of improved compositions of the above type, which have a pot life of enhanced duration, preferably longer than 48 hours.

Yet another object of this invention is the provision of improved compositions of the above type which, in their best embodiments, can be presented in a single pack having a storage stability of more than 6 months.

A further object of the present invention is the provision of improved compositions of the above type which crosslink at a temperature of from 50° to 200° C., preferably from 60° C. to 180° C., into an elastomeric coating exhibiting those desired properties of nonadhesiveness and/or water repellency.

Briefly, the present invention features novel polyorganosiloxane compositions that comprise:

(A) 100 parts by weight of a polydiorganosiloxane having silanol end groups;

(B) 0.1 to 25 parts by weight of a polyorganohydrosiloxane containing at least 3 SiH groups per molecule; and (C) a catalytically effective amount of a latent tin catalyst of the formula:

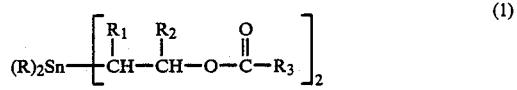

$$(R)_2Sn \left[ \begin{array}{c} R_1 \\ | \\ CH \end{array} - \begin{array}{c} R_2 \\ | \\ CH \end{array} - O - \begin{array}{c} O \\ \| \\ C \end{array} - R_3 \right]_2 \quad (1)$$

in which the radicals R, which may be identical or different, are linear or branched chain $C_1$-$C_{20}$ alkyl radicals, mononuclear aryl radicals, and arylalkyl and alkylaryl radicals, the alkyl moieties of which having from 1 to 6 carbon atoms; the radicals $R_1$ and $R_2$, which may be identical or different, are hydrogen atoms, cyano radicals, $C_1$-$C_6$ alkyl radicals, and alkoxycarbonyl radicals, the alkyl moieties of which having from 1 to 6 carbon atoms, with the proviso that R, and $R_2$ can together form a saturated hydrocarbon ring member having from 5 to 8 carbon atoms; and the radical $R_3$ is a hydrogen atom or a linear or branched chain $C_1$-$C_{20}$ alkyl radical.

DETAILED DESCRIPTION OF THE PREFERRED EMBODIMENTS OF THE INVENTION

More particularly according to the present invention, the preferred radicals R, $R_1$, $R_2$ and $R_3$ comprising the subject latent tin catalysts are the following:

| | |
|---|---|
| R | butyl, octyl and phenyl; |
| $R_1$ | H; |
| $R_2$ | H, methyl and cyano; |
| $R_3$ | H, methyl, undecanoyl, 2-ethylpentyl and nonyl. |

The preferred compounds corresponding to the formula (1) are the following:

Bis(2-acetoxyethyl)dibutyltin, formula (1): R=butyl, $R_1=R_2=H$, $R_3=$methyl;

Bis(2-acetoxyethyl)dioctyltin, formula (1): R=octyl, $R_1=R_2=H$, $R_3=$methyl;

Bis(2-lauroyloxyethyl)dibutyltin, formula (1): R=butyl, $R_1=R_2=H$, $R_3=$undecanoyl;

Bis(2-lauroyloxyethyl)dioctyltin, formula (1): R oc-tyl, $R_1=R_2=H$, $R_3=$undecanoyl;

Bis[2-(2-ethylhexanoyloxy)ethyl]dibutyltin, formula (1): R=butyl, $R_1=R_2=H$, $R_3=$2-ethylpentyl;

Bis[2-(2-ethylhexanoyloxy)ethyl]dioctyltin, formula (1): R=octyl, $R_1=R_2=H$, $R_3=$2-ethylpentyl;

Bis(2-decanoyloxyethyl)dibutyltin, formula (1): R=butyl, $R_1=R_2=H$, $R_3=$nonyl (in which the carbon in position 1 is quaternary);

Bis(2-acetoxy-2-methylethyl)dibutyltin, formula (1): R=butyl, $R_1=H$, $R_2=R_3=$methyl;

Bis(2-acetoxy-2-cyanoethyl)dibutyltin, formula (1): R=butyl, $R_1=H$, $R_2=CN$, $R_3=$methyl;

Bis(2-formyloxyethyl)dibutyltin, formula (1): R=butyl, $R_1=R_2=R_3=H$;

Bis(2-acetoxyethyl)diphenyltin, formula (1): R=phenyl, $R_1=R_2=H$, $R_3=$methyl; and Bis(2-lauroyloxyethyl)diphenyltin, formula (1): R=phenyl, $R_1=R_2=H$, $R_3=$undecanoyl.

The compounds of formula (1) may be prepared by addition reaction between a diorganotin dihydride of the formula (2):

$$R_2SnH_2 \quad (2)$$

in which the radicals R, which may be identical or different, are as defined above in respect of formula (1) and an enol carboxylate of the formula (3):

(3)

in which the radicals $R_1$, $R_2$ and $R_3$ are also as defined above in respect of formula (1).

The dihydrides of formula (2) are, for the most part, known compounds which are described in the literature. The novel such dihydrides may be prepared by reduction of the corresponding diorganotin dichloride with lithium aluminum hydride.

Another preparative process comprises reducing the corresponding diorganotin oxide with a polydiorganosiloxane bearing an SiH functional group, such as, for example, a polyhydromethylsiloxane blocked with a trimethylsilyl group at each end of the polymer chain.

The carboxylates of formula (3) are for the most part also known and described in the literature.

The vinyl carboxylates of formula:

(formula (3): $R_1=R_2=H$) are prepared by transesterification of vinyl acetate with the acid $R_3COOH$ in an acidic medium.

The enol carboxylates of the formula:

(formula (3): $R_1=H$, $R_3=CH_3$) are prepared by reaction of the ketone $H_3C-COR_2$ with isopropenyl acetate in an acidic medium.

The hydrostannation reaction between a compound of formula (2) and a compound of formula (3) is preferably carried out by reacting one mole of the compound of formula (2) with two moles of the compound of formula (3) at ambient temperature in a hydrocarbon organic solvent, such as cyclohexane. The reaction mixture is subjected to UV radiation (360 nm).

The hydrostannation reaction can also be carried out without solvent in the presence of a free-radical generator such as, for example, in the presence of AIBN (azobisisobutyronitrile) at a temperature of 70°–80° C.

The tin compounds of formula (1), which are generally liquids at ambient temperature, may be identified by the analytical techniques of IR (infrared) and NMR ($^{119}$Sn, $^{13}$C and $^1$H nuclear magnetic resonance) spectroscopy, as well as by mass spectroscopy and by measurement of the Môssbauer effect.

It would appear, however, that in the present state of the art of techniques, the $^{119}$Sn NMR analytical method such as described, in particular, in the paper by Peter J. Smith, "Chemical Shifts of $^{119}$Sn Nuclei in Organotin Compounds", page 291 et seq., published in the *Annual Reports on NMR Spectroscopy*, volume 8, Academic Press (1978), is a method which is itself sufficiently precise to characterize the various tin compounds present in a mixture, in particular a reaction mixture, and to enable the chemical formulae of most of these compounds to be established.

The fundamental parameter determined by $^{119}$Sn NMR is the value of the chemical shift, expressed in parts per million relative to a reference (generally tetramethyltin).

The value of the chemical shift δ is especially sensitive to the electronegativity of the groups borne by the tin and to the change in the coordination number of the tin atom. Specific examples of the characterization of organostannic derivatives on the basis of $^{119}$Sn NMR are described, in particular, by A. G. Davies and P. J. Smith, *Comprehensive Organo-Metallic Chemistry*, 11, Tin, pages 523 to 529 and J. Otera, *J. of Organomet. Chem.*, 221, pages 57–61 (1981).

The compounds of formula (1) are stable at ambient temperature and are inactive as catalysts for curing organopolysiloxane compositions.

On the other hand, the compounds of formula (1), when subjected to an elevated temperature, decompose thermally to well-known compounds, namely, the corresponding diorganotin dicarboxylates with release of the corresponding ethylenically unsaturated compound according to the equation:

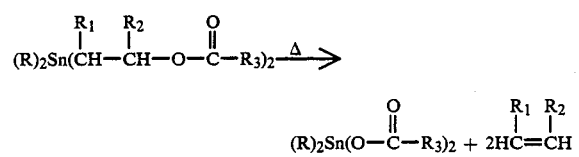

The thermal decomposition of the compounds of formula (1) takes place at a temperature which is specific for each of the compounds. This temperature generally ranges from 50° to 250° C.

The diorganotin dicarboxylate released is then an active catalyst for the curing or hardening of organopolysiloxane compositions.

The advantage of the latent catalysts of formula (1) is, therefore, the option of mixing the starting materials with the latent catalyst without the reaction being catalyzed, and to initiate the catalysis of the reaction by heating the mixture to the decomposition temperature of the latent catalyst.

Accordingly, the present invention also features a process for crosslinking a polyorganosiloxane composition, comprising admixing the polymers (A) and (B) and a catalytically effective amount of a latent catalyst (C) of formula (1) at ambient temperature, and then heating the mixture to a temperature equal to or higher than the thermal decomposition temperature of the latent catalyst, possibly with evaporation of the solvent or of the water which may be present in the mixture.

The decomposition temperature of the catalyst generally ranges from 60° to 200° C. It depends on the individual latent catalyst which is employed and on the form of the polyorganosiloxane composition.

This decomposition temperature may be lowered by the addition of an effective amount of a nucleophilic agent selected, for example, from among water, a secondary organic amine, an organic alcohol, an organosilicon compound containing a silanol functional group and an organic compound containing a mercapto (SH) functional group. By "effective amount" of a nucleophilic agent is intended from 0.001 to 10 moles and more of nucleophilic agent per mole of the tin compound of formula (1).

Thus, in the case of the solvent-free polyorganosiloxane compositions and of those in solution in an organic solvent, this decomposition temperature is close to the intrinsic decomposition temperature which is specific to the latent catalyst. In the case of these two types of compositions, it is often possible to package the compositions in a single pack having a storage stability period which ca exceed 6 months.

On the other hand, in the case of the aqueous emulsion compositions, this decomposition temperature can be lowered to ambient temperature in certain cases. It is then generally desirable to package the emulsion in at least two packs and, in this case, the pot-life period of the composition is appreciably improved in relation to that of the compositions containing a known tin catalyst (in particular dialkyltin dicarboxylates).

By "effective amount" of the latent catalyst is generally intended a content of 0.001 to 6 parts, preferably from 0.01 to 3 parts (calculated as the weight of tin metal) of latent catalyst of formula (1) per 100 parts by weight of the total solids contents of the polymers (A) and (B).

The coating compositions according to the invention generally contain no inorganic fillers. However, the presence of fillers, preferably siliceous (precipitated silica, pyrogenic silica, diatomaceous earths, ground quartz, and the like) which are generally employed in silicone elastomer compositions is also within the scope of the invention, in a proportion of 1 to 50 parts of filler per 100 parts of polymer (A).

The polymers (A) and (B) have long been known to this art and are described, in particular, in the aforementioned patents.

The polymers (A) may be selected from among polydimethylsiloxanes containing terminal hydroxyl groups (with silanol endgroups), having a viscosity of at least 10 mPa.s at 25° C. These polymers (A) comprise relatively nonviscous oils ranging, for example, from 10 mPa.s to 5000 mPa.s, viscous oils ranging from 5000 to $10^6$ mPa.s, and resins having a viscosity above $10^6$ mPa.s.

The polymers (B) may be linear, cyclic or branched.

The substantially linear or branched polymers (B) contain recurring structural units of the average general formula:

$$R_xH_ySiO_{(4-x-y)/2}$$

in which the radicals (R), which may be identical or different, are as defined above, except that it is possible that certain of the radicals R may be vinyl radicals. Preferably at least 80% of the radicals R are methyl radicals.

The symbol x denotes any number ranging from 1 to 1.99, the symbol y denotes any number ranging from 1.1 to 0.7, with the sum x+y ranging from 1.7 to 2.6. Methylhydropolysiloxanes are preferably employed as organohydropolysiloxanes (B).

With regard to the branched polymers (B), each of these comprises a combination of recurring units selected from among those of formulae $R_3SiO_{0.5}$, $R_2SiO$, $RSiO_{1.5}$, $SiO_2$, $HR_2SiO_{0.5}$, $HRSiO$ and $HSiO_{1.5}$; each combination which defines a polymer includes at least one recurring unit selected from among those of formulae $RSiO_{1.5}$, $SiO_2$ and $HSiO_{1.5}$, the units being distributed in such manner, however, that the average formula of each polymer, reduced to one silicon, is included within the above-mentioned average general formula.

The viscosity of these polymers ranges from 2 mPa.s at 25° C. to 10,000 mPa.s at 25° l C.

In the case where the composition is employed without a solvent, the viscosity of the polymers (A) and (B) is selected such that the viscosity of the mixture, that is to say, of the composition, ranges from 40 to 5000 mPa.s, preferably from 100 to 3000 mPa.s at 25° C.

The compositions according to the invention can be emulsified, dispersed or diluted in water or dissolved in a volatile organic solvent which is compatible with the composition and selected, for example, from among the alkanes, petroleum cuts containing paraffinic compounds, toluene, heptane, xylene, isopropanol, methyl isobutyl ketone, tetrahydrofuran, chlorobenzene, chloroform, 1,1,1-trichloroethane and monoethylene glycol and methylene glycol derivatives.

Water, or the solvent, preferably constitutes from 50 to 99% by weight of the dispersion or of the solution at the time of use.

During the crosslinking treatment involving the evaporation of the water or of the solvent, the composition cures and it can therefore be used as a coating composition for flexible supports made of metal, paper, plastic, cardboard and the like.

The compositions according to the invention are preferably employed as compositions for rendering a material, such as sheets of metal, glass, plastics or paper, nonadhesive to other materials to which it would normally adhere.

This invention, therefore, also features a process which makes it possible to render sheets of flexible material nonadhesive to surfaces to which they normally adhere, which process is characterized in that it comprises applying a quantity of composition in accordance with the invention, generally comprising from 0.1 to 10 g per m² of surface area and in coating and in crosslinking the composition by heating as indicated above.

The gel times (pot-life period) of these diluted and undiluted compositions at ambient temperature can be more than several weeks, in most cases several months.

The solvent-free, that is to say, undiluted, compositions are applied with the aid of devices capable of uniformly depositing small amounts of liquids. For example, the device may be used known as a "kiss roll coater" comprising, in particular, two superposed rolls: the function of the lower roll, immersed in the coating trough where the compositions are placed, is to impregnate the upper roll with a very thin layer and the function of the latter roll is then to deposit onto the paper the desired quantities of the compositions with which it is impregnated. Metering of this type is obtained by adjusting the relative speed of the two rolls which rotate in opposite directions. The coating machine described in French Patent No. FR-A-2,294,765 can also be employed.

The dilute compositions, namely, those with a solvent or in aqueous emulsion, can be applied with the aid of the devices employed on industrial papercoating machines such as the "multi-dot" gravure roll and the system known as "reverse roll". Once deposited onto the substrates, the compositions are cured by an energy input, at least a part of which may be supplied by a UV radiation in a few seconds by passing same under a UV light, and in tunnel ovens heated to about 60°–200° C.; the residence time in these ovens generally varies from 2 to 30 seconds. For a given oven length, it is a function of the speed at which the coated substrates travel (this speed can exceed 200 meters per minute).

The amounts of compositions deposited on the substrates can vary and in most cases range from 0.1 to 10 g/m² of the area treated. These amounts depend on the nature of the substrates and the required antiadhesive properties. In most cases, they range from 0.5 to 1.5 g/m² in the case of nonporous substrates.

As is apparent, the aqueous emulsion compositions which are typically packaged as a component (I) containing (A) and (C) and a component (II) containing (B), comprise the usual emulsifying or dispersing agents which may be anionic, nonionic or cationic.

The nonionic polymeric materials, such as polyvinyl alcohol (Rhodoviol® 25/140 marketed by Rhône-Poulenc, or Elvanol® 50-42 marketed by Du Pont) are particularly suitable for component (I).

Furthermore, polyalkylene glycol alkyl ethers and alkylphenyl ethers (for example, Cemulsol® O.N. 10-20 marketed by Rhône-Poulenc or Tergitol® NP-40 marketed by Union Carbide) are more particularly suitable for component (II).

In order to further illustrate the present invention and the advantages thereof, the following specific examples are given, it being understood that same are intended only as illustrative and in nowise limitative.

In said examples to follow, as well as in the description given above, all viscosities were measured at 25° C. and all parts and percentages are given by weight, unless otherwise indicated.

EXAMPLE 1

Preparation and decomposition of bis(2-acetoxyethyl)dibutyltin:

(a) Preparation of dibutyltin dihydride: $(C_4H_9)_2SnH_2$ 10.35 g of lithium aluminum hydride were introduced into a 1-liter three-necked round-bottomed flask and 250 ml of anhydrous ether were added dropwise thereto, under nitrogen and under magnetic stirring; 52.1 g of dibutyltin dichloride, dissolved in 100 ml of anhydrous ether, were then added dropwise. The reaction was exothermic. Upon completion of the addition, the reaction mixture was heated under reflux for 2 hours, 30 min.

500 mg of hydroquinone and 100 ml of pentane were then added in succession. The mixture was then cooled to 0° C. and was then hydrolyzed slowly.

The organic phase was recovered and was dried over magnesium sulfate. The solvents were removed at ambient temperature under a vacuum of 2.7 kPa.

The dibutyltin dihydride was distilled under a vacuum of 0.0013 kPa at 35° C. at the head of the column.

The reaction yield was 70% as dibutyltin dihydride: $(C_4H_9)_2SnH_2$; bp=35° C. at 0.0013 kPa.

Spectral characteristics:
$^1$H NMR (pure$\delta$(ppm))=4.6 (2 H, m); 1.65 - 0.9 (18 H, m).
$^{119}$Sn NMR $(C_6D_6$, internal $(CH_3)_4Sn)\delta=204.0$ ppm; $|^1J(SnH)|=1676$ Hz; $|^2J(SnH)|=56$ Hz.
IR (film): $\nu(SnH)=1840$ cm$^{-1}$ (S).

(b) Preparation of bis(2-acetoxyethyl)dibutyltin:

2.349 g (0.01 mole) of dibutyltin dihydride, 1.722 g (0.02 mole) of distilled vinyl acetate and 2 g of anhydrous cyclohexane were introduced into a Pyrex® vessel thermostated at 25° C. The solution was exposed to ultraviolet rays for 3 hours. The cyclohexane was then removed under vacuum at ambient temperature. The expected product was obtained pure in quantitative yield.

This operating procedure was the same in all the cases of addition of dibutyltin dihydride to an unsaturated compound. Only the temperature and the exposure times were varied.

The product obtained had the following formula:

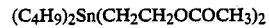

$(C_4H_9)_2Sn(CH_2CH_2OCOCH_3)_2$

Spectral characteristics:
$^1$H NMR (CCl$_4$, int. TMS)$\delta$(ppm)=4.7 - 3.75 (4 H, m); 1.95 (6 H, s); 1.7 - 0.9 (22 H, m).
$^{119}$Sn NMR $(C_6D_6$, internal $(CH_3)_4Sn)\delta=-19.8$ ppm.
IR (film):$\nu(CO)=1740$ cm$^{-1}$ (S).

(c) Decomposition of bis(2-acetoxyethyl)dibutyltin:

1.84 g of bis(2-acetoxyethyl)dibutyltin were placed in a test tube connected to a water trough. The tube was placed in an oil bath thermostated at 110° C. At the end of 2 hours, 30 min, 200 cm³ of gas were recovered and identified by IR spectroscopy; the spectrum of this gas was identical with that of ethylene (fine and intense characteristic band at 950 cm$^{-1}$). The liquid produced by the decomposition of the starting material (1.59 g) was distilled under a vacuum of 0.013 kPa at 90° C. at the head of the column. The product obtained was dibutyltin diacetate of the formula:

$(C_4H_9)_2Sn(OCOCH_3)_2$; bp=90° C. at 0.013 kPa.

Spectral characteristics:
$^1H$ NMR $(CCl_4$, int. TMS)$\delta$(ppm)=2.0 (6 H, s); 1.65 - 0.9 (18 H, m).
$^{119}Sn$ NMR $(C_6D_6$, internal $(CH_3)_4Sn$) $\delta = -156.3$ ppm.
IR (film):$\nu(CO)$=1605; 1570; 1425 cm$^{-1}$ (S).

EXAMPLE 2

Preparation and decomposition of bis(2acetoxyethyl)dioctyltin:

This preparation required the preliminary synthesis of dioctyltin dihydride $(C_8H_{17})_2SnH_2$.

(a) Preparation of dioctyltin dihydride:

The operating procedure followed was the same as that employed in Example 1 for the synthesis of dibutyltin dihydride, except that the starting material was dioctyltin dichloride.

The product was obtained pure after distillation using a bulb tube, under a vacuum of $2 \times 10_{-2}$ kPa at 90° C. (oven temperature).

Spectral characteristics:
$^1H$ NMR (pure)$\delta$(ppm)=4.6 (2 H, m); 1.65 - 0.9 (34 H, m).

(b) Preparation of bis(2-acetoxyethyl)dioctyltin:

The product was obtained in the same manner as its homolog in the dibutyl series: bis(2-acetoxyethyl)dibutyltin of Example 1.

The product had the following formula:

$(C_8H_{17})_2Sn(CH_2CH_2OCOCH_3)$ 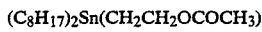

Spectral characteristics:
$^1H$ NMR $(CCl_4$, int. TMS)$\delta$(ppm)=4.65 - 3.7 (4 H, m); 1.95 (6 H, s); 1.65 - 0.9 (38 H, m).
$^{119}Sn$ NMR $(C_6D_6$, internal $(CH_3)_4Sn$) $\delta = -20.4$ ppm.

(c) Decomposition of bis(2-acetoxyethyl)dioctyltin:

The decomposition of the pure product was complete after 3 hours at 110° C.

The product obtained was dioctyltin diacetate of the formula:

$(C_8H_{17})_2Sn(OCOCH_3)_2$

Spectral characteristics:
$^1H$ NMR $(CCl_4$, int. TMS)$\delta$(ppm)=2.0 - 0.9 (40 H, m).
$^{119}Sn$ NMR $(C_6D_6$, internal $(CH_3)_4Sn$)$\delta = -156.8$ ppm.

EXAMPLE 3

Preparation and decomposition of bis(2-lauroyloxyethyl)dibutyltin:

(a) Preparation of vinyl laurate:

51.5 g of vinyl acetate and 20 g (0.1 mole) of lauric acid were introduced into a 100-ml two-necked round-bottomed flask. The acid was dissolved by warming and 0.4 g of mercuric acetate was added under a stream of nitrogen. The mixture was thus maintained for 30 minutes at ambient temperature, with magnetic stirring, under nitrogen. Two drops of sulfuric acid (95%) were  then added and the reaction mixture was heated under reflux for 3 hours. It was then permitted to cool to ambient temperature and 0.21 g of sodium acetate was then added.

The excess vinyl acetate was recovered by distillation at atmosphere pressure.

The vinyl laurate was distilled under a vacuum of 0.013 kPa at 94° C. at the head of the column.

The product was obtained in a 70% yield. Its formula was the following:

$H_2C=CHOCOC_{11}H_{23}$; bp=94° C. at 0.013 kPa. 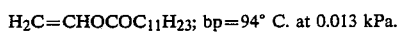

Spectral characteristics:
$^1H$ NMR $(CCl_4$, int. TMS)$\delta$(ppm)=7.2 (1 H, dd); 4.75 (1 H, dd); 4.45 (1 H, dd); 2.3 (2 H, t); 1.9 - 0.9 (21 H, m).

(b) Preparation of bis(2-lauroyloxyethyl)dibutyltin:

The operating procedure followed was the same as in Example 1. Vinyl acetate was replaced with 4.526 g (0.02 mole) of vinyl laurate. The solution was exposed to ultraviolet rays for 4 hours.

The product, obtained quantitatively, had the following formula:

$(C_4H_9)_2Sn(CH_2CH_2OCOC_{11}H_{23})_2$

Spectral characteristics:
$^1H$ NMR $(CCl_4$, int. TMS)$\delta$(ppm)=4.65 - 3.75 (4 H, m); 2.2 (4 H, t); 1.9 - 0.9 (4 H, m).
$^{119}Sn$ NMR $(C_6D_6$, internal $(CH_3)_4Sn)\delta = -20.0$ ppm.
IR (film): $\nu(CO)$=1740 cm$^{-1}$ (F). 

(c) Decomposition of bis(2-lauroyloxyethyl)dibutyltin:

The decomposition was carried out as in Example 1. At 140 C, it was complete after 2 hours, 30 min.

The decomposition product was identified as being dibutyltin dilaurate of the formula:

$(C_4H_9)_2Sn(OCOC_{11}H_{23})_2$

Spectral characteristics:
$^1H$ NMR $(CCl_4$, int. TMS)$\delta$(ppm)=2.2 (4 H, t); 1.6 - 0.9 (60 H, m).
$^{119}Sn$ NMR $(C_6D_6$, internal $(CH_3)_4Sn)\delta = 152.5$ ppm.

EXAMPLE 4

Preparation and decomposition of bis(2-lauroyloxyethyl)dioctyltin:

(a) Preparation of bis(2-lauroyloxyethyl)dioctyltin:

The product was obtained by hydrostannation of vinyl laurate. The solution was exposed to ultraviolet rays for 7 hours. The product had the following formula: 

Spectral characteristics:

$^1H$ NMR $(CCl_4$, int. TMS) $\delta$(ppm)=4.6 - 3.9 (4 H, m); 2.4 -0.9 (84 H, m).
$^{119}Sn$ NMR $(C_6D_6$, internal $(CH_3)_4Sn)\delta = 20.6$ ppm.

(b) Decomposition of bis(2-lauroyloxyethyl)dioctyltin:

This was carried out under the same conditions as that of bis(2-lauroyloxyethyl)dibutyltin and produced dioctyltin dilaurate:

$(C_8H_{17})_2Sn(OCOC_{11}H_{23})_2$ 

$^1$H NMR (CCl$_4$, int. TMS)$\delta$(ppm)=2.4 - 0.9 (80 H, m).

EXAMPLE 5

Preparation and decomposition of bis[2-(2-ethylhexanoyloxy)ethyl]dibutyltin:

(a) Preparation of bis[2-(2-ethylhexanoyloxy)ethyl]dibutyltin:

2.349 g (0.01 mol) of dibutyltin dihydride, 3.405 g (0.02 mol) of distilled vinyl 2-ethylhexanoate and 2.5 g of anhydrous cyclohexane were introduced into a Pyrex ® tube. The exposure to ultraviolet rays was for 8 hours 30 min at 30°–35° C. The solvent was removed under vacuum at ambient temperature.

The reaction product, obtained quantitatively, was the following:

$(C_4H_9)_2Sn[CH_2CH_2OCOCH(C_2H_9)]_2$

Spectral characteristics:
$^1$H NMR (CCl$_4$, int. TMS)$\delta$(ppm)=4.7 - 4 (4 H, m); 2.4 - 0.9 (52 H, m).
$^{119}$Sn NMR (C$_6$D$_6$, internal (CH$_3$)$_4$Sn) $\delta$=−20.9 ppm.
IR (film): $\nu$(CO)=1735 cm$^{-1}$ (S).

(b) Decomposition of bis[2-(2-ethylhexanoyloxy)ethyl]dibutyltin:

The decomposition was carried out as in Example 1. It was complete after 5 hours at 140 C. The product obtained was identified as being:

$(C_4H_9)_2Sn[OCOCH(C_2H_5)(C_4H_9)]_2$

Spectral characteristics:
$^1$H NMR (CCl$_4$, int. TMS)$\delta$(ppm)=2.5 - 0.9 (48 H, m).
$^{119}$Sn NMR (C$_6$D$_6$, internal (CH$_3$)$_4$Sn) $\delta$=−154.9 ppm.

EXAMPLE 6

Preparation and decomposition of bis[2-(2-ethylhexanoyloxy)ethyl]dioctyltin:

(a) Preparation of bis[2-(2-ethylhexanoyloxy)ethyl]dioctyltin:

The addition of dioctyltin dihydride to vinyl 2-ethylhexanoate was carried out in the same manner as that of dibutyltin dihydride (Example 5).

It was complete after 13 hours of exposure of the reaction mixture to ultraviolet rays.

The product, obtained quantitatively, had the formula:

$(C_8H_{17})_2Sn[CH_2CH_2OCOCH(C_2H_5)(C_4H_9)]_2$

Spectral characteristics:
$^1$H NMR (CCl$_4$, int. TMS) $\delta$(ppm)=4.7 - 4.0 (4 H, m); 1.6 -0.9 (68 H, m).
$^{119}$Sn NMR (C$_6$D$_6$, internal (CH$_3$)$_4$Sn)$\delta$=21.7 ppm.

(b) Decomposition of bis2-(2-ethylhexanoyloxy)ethyl]dioctyltin:

This was carried out under the same conditions as those of the homolog in the dibutyl series (Example 5).

The decomposition product had the following formula:

$(C_8H_{17})_2Sn[OCOCH(C_2H_5)(C_4H_9)]_2$

Spectral characteristics:
$^1$H NMR (CCl$_4$, int. TMS)$\delta$(ppm)=2.5 - 0.9 (64 H, m).
$^{119}$Sn NMR (C$_6$D$_6$, internal (CH$_3$)$_4$Sn)$\delta$=−157.9 ppm.

EXAMPLE 7

Preparation and decomposition of bis(2-decanoyloxvethyl)dibutyltin (also designated bis(2-versatoyloxvethyl)dibutyltin):

(a) Preparation of vinyl versatate (also designated vinyl decanoate):

Versatic acid ® 10 (Shell) is a mixture of acids of empirical formula C$_{10}$H$_{20}$O$_2$ in which at least 98% of the weight thereof has a quaternary carbon atom in an alpha position with respect to the acid functional group. The radical R$_3$ of the formula (1) can therefore be likened to a nonyl radical.

The operating procedure was the same as for the preparation of vinyl laurate. Vinyl versatate was obtained by distillation in a 60% yield.

$H_2C=CHOCOC_9H_{19}$; bp=100° C. at 3.3 kPa.

Spectral characteristics:
$^1$H NMR (CCl$_4$, int. TMS)$\delta$(ppm)=7.33 (1 H, dd); 4.78 (1 H, dd); 4.45 (1 H, dd); 2.0 - 0.8 (19 H, m).

(b) Preparation of bis(2-versatoyloxvethyl)dibutyltin:

The operating procedure of Example 1 was repeated. The vessel was themostated at 0° C. The solution was exposed to ultraviolet rays for 2 hours. The expected product was obtained quantitatively; its formula was as follows:

$(C_4H_9)_2Sn(CH_2CH_2OCOC_9H_{19})_2$

Spectral characteristics:
$^1$H NMR (CCl$_4$, int. TMS)$\delta$(ppm)=4.5 - 4.0 (4 H, m); 2.0 -0.8 (60 H, m).
$^{119}$Sn NMR (C$_6$D$_6$, internal (CH$_3$)$_4$Sn)$\delta$=−22.3 ppm.
IR (film): $\nu$(CO)=1730 cm$^{-1}$ (S).

(c) Decomposition of bis(2-versatoyloxvethyl)dibutyltin:

The decomposition was conducted as in Example 1. At 140 C, 65% of the product had disappeared after 4 hours (percentage estimated by $^{119}$Sn NMR). The decomposition product was dibutyltin diversatate:

$(C_4H_9)_2Sn(OCOC_9H_{19})_2$

Spectral characteristics:
$^1$H NMR (CCl$_4$, int. TMS)$\delta$(ppm)=2.0 - 0.8 (56 H, m).
$^{119}$Sn NMR (C$_6$D$_6$, internal (CH$_3$)$_4$Sn)$\delta$=−162.6 ppm.

EXAMPLE 8

Preparation and decomposition of bis(2-acetoxy-2-methylethyl)dibutyltin:

(a) Preparation of bis(2-acetoxy-2-methylethyl)dibutyltin:

The operating procedure was the same as in Example 7 in the case of the addition to vinyl versatate; here it was replaced by 2.002 g (0.02 mole) of isopropenyl acetate. The reaction mixture was exposed to ultraviolet rays for 3 hours, 30 min, at 0° C. The product, obtained quantitatively, had the following formula:

$(C_4H_9)_2Sn[CH_2CH(CH_3)OCOCH_3]_2$

Spectral characteristics:
$^1$H NMR (CCl$_4$, int TMS) δ(ppm)=5.6 - 4.6 (2 H, m); 1.95 (6 H, s); 1.8 - 0.9 (28 H, m).
$^{119}$Sn NMR (C$_6$D$_6$, internal (CH$_3$)$_4$Sn)δ=−24.9 ppm.

(b) Decomposition of bis(2-acetoxy-2-methylethyl)dibutyltin:

The pure product, placed in a test tube, was heated to 80° C. After a quarter of an hour, the decomposition was complete. Dibutyltin diacetate was obtained pure. Its characteristics are reported at the end of Example 1.

EXAMPLE 9

Preparation and decomposition of bis(2-acetoxy-2-cyanoethyl)dibutyltin:

(a) Preparation of bis(2-acetoxy-2-cyanoethyl)dibutyltin:

The addition of dibutyltin dihydride to 1-cyanovinyl acetate was conducted according to the operating procedure of Example 1. The exposure to ultraviolet rays was for 5 hours. The product obtained was identified as being bis(2-acetoxy-2-cyanoethyl)dibutyltin, of the formula:

$(C_4H_9)_2Sn[CH_2CH(CN)OCOCH_3]_2$

Spectral characteristics:
$^1$H NMR (CCl$_4$, int. TMS)δ(ppm)=5.4 (2 H, t); 2.1 (6 H, s); 1.65 - 0.9 (22 H, m). $^{119}$Sn NMR (C$_6$D$_6$, internal (CH$_3$)$_4$Sn) δ=22.6 ppm.

(b) Decomposition of bis(2-acetoxy-2-cyanoethyl)dibutyltin:

The decomposition was carried out as in Example 1 at 110° C.; at the end of 2 hours a mixture of dibutyltin diacetate and acrylonitrile was obtained, without any trace of the starting material.

Spectral characteristics of acrylonitrile: $H_2C=CHCN$
$^1$H NMR (CCl$_4$, int. TMS)δ(ppm)=6.4 - 5.4.
For those of $(C_4H_9)_2Sn(OCOCH_3)_2$: see Example 1.

EXAMPLE 10

Preparation and decomposition of bis(2-formyloxyethyl)dibutyltin:

(a) Preparation of vinyl formate:

The operating procedure followed was the same as that of Example 3 for the preparation of vinyl laurate. The distillation was carried out using a Cadiot apparatus (50-cm spinning band column). The product obtained had the following formula:

$H_2C=CHOCOH$; bp=45° C. at 100 kPa.

Spectral characteristics:
$^1$H NMR (CCl$_4$, int. TMS)δ(ppm)=8.05 (1 H, s); 7.32 (1 H, dd); 4.95 (1 H, dd); 4.65 (1 H, dd).

(b) Preparation and decomposition of bis(2-formyloxyethyl)dibutyltin:

The addition of dibutyltin dihydride to vinyl formate was carried out in a Pyrex® tube at 30°-35° C. by following the operating procedure of Example 5. The product was not isolated, because it decomposed as it was being formed.

Only the spectral characteristics of dibutyltin diformate are reported here: $(C_4H_9)_2Sn(OCOH)_2$
$^1$H NMR (CCl$_4$, int. TMS)δ(ppm)=8.25 (2 H, s); 1.8 - 0.9 (18 H, m).
$^{119}$Sn NMR (C$_6$D$_6$, internal (CH$_3$)$_4$Sn)δ=−102.5 ppm.

EXAMPLE 11

Preparation and decomposition of bis(2-acetoxyethyl)diphenyltin:

(a) Preparation of diphenyltin dihydride:

The operating procedure followed was the same as that employed in Example 1 for the synthesis of dibutyltin dihydride. The product was sensitive; it required a distillation in clean glassware (grease-free ground joints). The latter was carried out in a bulb tube, under a vacuum of 0.27 kPa, at 100°-110° C. (oven temperature).

(b) Preparation of bis(2-acetoxyethyl)diphenyltin:

Diphenyltin dihydride and vinyl acetate were introduced in stoichiometric amount into a Pyrex® tube containing anhydrous cyclohexane. The reaction mixture was exposed to ultraviolet rays for 1 hour at 30° C. The solvent was then removed under vacuum at ambient temperature. The product, obtained quantitatively, had the following formula:

$(C_6H_5)_2Sn(CH_2CH_2OCOCH_3)_2$

Spectral characteristics:
$^1$H NMR (CCl$_4$, int. TMS)δ(ppm)=7.6 - 6.9 (10 H, m); 4.75 -3.7 (4 H, m); 1.75 - 0.9 (10 H, m).

(c) Decomposition of bis(2-acetoxyethyl)diphenyltin:

The decomposition of the pure product was complete after 1 hour at 150° C. and produced diphenyltin diacetate of the formula:

$(C_6H_5)_2Sn(OCOCH_3)_2$

Spectral characteristics:
$^1$H NMR (CCl$_4$, int. TMS)δ(ppm)=7.9 - 7.0 (10 H, m); 1.8 (6 H, s).

EXAMPLE 12

Preparation and decomposition of bis(2-lauroyloxyethyl)diphenyltin:

(a) Preparation of bis(2-lauroyloxyethyl)diphenyltin:

The product was obtained under the same conditions as previously in Example 12. The product had the following formula:

$(C_6H_5)_2Sn(CH_2CH_2OCOC_{11}H_{23})_2$

Spectral characteristics:
$^1$H NMR (CCl$_4$, int. TMS)$\delta$(ppm)=7.5 - 6.9 (10 H, m); 4.75 -3.7 (4 H, m); 2.2 - 0.75 (50 H, m).

(b) Decomposition of bis(2-lauroyloxyethyl)diphenyltin:

At the end of 1 hour at 150° C., the product had disappeared; diphenyltin dilaurate was obtained:

$(C_6H_5)_2Sn(OCOCH_{11}H_{23})_2$

Spectral characteristics:
$^1$H NMR (CCl$_4$, int. TMS)$\delta$(ppm)=7.75 - 7.0 (10 H, m); 2.2 -0.75 (46 H, m).

EXAMPLE 13

The following mixture was homogenized:

(i) 90 parts of an ($\alpha,\omega$-dihydroxy)polydimethylsiloxane resin having a viscosity of $30\times10^6$ mPa.s;

(ii) 210 parts of an ($\alpha,\omega$-dihydroxy)polydimethylsiloxane oil having a viscosity of 100 mPa.s;

(iii) 14 parts of a polyhydromethylsiloxane having trimethylsiloxyl end groups with a viscosity of 20 mPa.s;

(iv) 686 parts of xylene; 4,000 parts of hexane were added to 1,000 parts of the above bath.

To 5,000 parts of the composition obtained, there were added: 20 parts of a product formed by the addition, mole per mole, of $\gamma$-aminopropyltriethoxysilane and $\gamma$-glycidoxypropyltrimethoxysilane; and 1.75 parts of bis(2-acetoxyethyl)dibutyltin prepared in Example 1.

The mixture was stirred vigorously at ambient temperature (20° C.) for a few minutes and this mixture was then deposited (approximately from 1 to 3 g/m$^2$) onto Glacine Sibille ® 9 562 paper by means of a Meyer No. 10 coating bar and the silicon composition was cured for 30 seconds in an oven with forced air circulation, set at 150° C. The crosslinking was complete and excellent in quality.

EXAMPLES 14 TO 15 AND COMPARATIVE EXAMPLE 16

The operating procedure of Example 13 was repeated exactly, except that:

in Example 14: 1.75 parts of the latent catalyst of Example 13 were replaced with 1.85 parts of bis(2-acetoxy-2-methylethyl)dibutyltin prepared in Example 8;

in Example 15: 1.75 parts of the latent catalyst of Example 13 were replaced with 2.95 parts of bis(2-lauroyloxyethyl)dibutyltin prepared in Example 3;

in Example 16: 1.75 parts of the latent catalyst of Example 13 were replaced with 2.45 parts of bis[2-(2-ethylhexanoyloxy)ethyl]dibutyltin prepared in Example 5;

in comparative Example 16: 1.75 parts of the latent catalyst of Example 13 were replaced with 1.50 parts of dibutyltin dicarboxylate.

As in Example 13, the crosslinking was complete and excellent in quality and similar for equivalent amounts of tin compound.

EXAMPLE 17

This example illustrates the pot life obtained with the latent catalysts and the corresponding active catalyst for the composition resulting from mixing the following in open air:

(i) 23 parts of $\alpha,\omega$-dihydroxypolydimethylsiloxane oil having a viscosity of 14,000 mPa.s;

(ii) 1 part of a polyhydromethylsiloxane oil having trimethylsiloxyl end groups at a viscosity of 20 mPa.s; and (iii) 0.712 millimoles of tin compound X.

The stability of the mixtures in open air was determined by measuring the time required for each of the mixtures to reach 150,000 mPa.s at 20° C. This was carried out using a Carri-Med ® rheometer fitted with a cone/plate system thermostated at 20° C.

The results obtained are reported in the Table below.

TABLE

| TIN COMPOUND | TIME (hours) |
| --- | --- |
| (C$_4$H$_9$)$_2$ Sn(OCOCH$_3$)$_2$ | 0.10 |
| (C$_4$H$_9$)$_2$ Sn(CH$_2$CH$_2$OCOCH$_3$)$_2$ | 312 |
| C$_4$H$_9$)$_2$ Sn(CH$_2$CH(CH$_3$)OCOCH$_3$)$_2$ | 20 |
| (C$_4$H$_9$)$_2$ Sn(OCOC$_{11}$H$_{23}$)$_2$ | 0.13 |
| (C$_4$H$_9$)$_2$ Sn(CH$_2$CH$_2$OCOC$_{11}$H$_{23}$)$_2$ | 132 |
| (C$_4$H$_9$)$_2$[SnOCOCH(C$_2$H$_5$)(C$_4$H$_9$)]$_2$ | 0.27 |
| (C$_4$H$_9$)$_2$[SnCH$_2$CH$_2$OCOCH(C$_2$H$_5$)(C$_4$H$_9$)]$_2$ | 228 |
| 0 | 330 |

From the Table, it will be appreciated that the mixtures comprising a latent catalyst according to the invention exhibit a pot life which can be very close to the control mixture without a catalyst (330 hours), and always much lunger than the mixtures containing their thermal decomposition product.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A storage-stable polyorganosiloxane composition comprising:
   (A) 100 parts by weight of a polydiorganosiloxane having silanol endgroups;
   (B) 0.1 to 25 parts by weight of a polyorganohydrosiloxane containing at least 3 SiH groups per molecule; and
   (C) a catalytically effective amount of a latent tin catalyst of the formula:

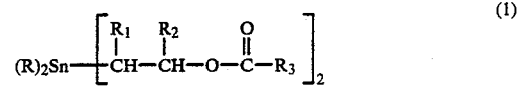

(1)

in which the radicals R, which may be identical or different, are linear or branched chain C$_1$-C$_{20}$ alkyl radicals, mononuclear aryl radicals, arylalkyl or alkylaryl radicals, the alkyl moieties of which having from 1 to 6 carbon atoms; the radicals R$_1$ and R$_2$, which may be identical or different, are hydrogen atoms, cyano radicals, C$_1$-C$_6$ alkyl radicals or alkoxycarbonyl radicals, the alkyl moieties of which having from 1 to 6 carbon atoms, with the proviso that R$_1$ and R$_2$ may together form a saturated hydrocarbon ring member containing from 5 to 8 carbon atoms; and the radical R$_3$ is a hydrogen atom or a linear or branched chain C$_1$-C$_{20}$ alkyl radical.

2. The polyorganosiloxane composition as defined by claim 1, comprising from 0.001 to 6 parts by weight of latent catalyst (C) per 100 parts by weight of the total solids content of the polymers (A) and (B).

3. The polyorganosiloxane composition as defined by claim 1, in solvent-free state, and wherein the viscosity of the constituents (A) and (B) is such that the viscosity of said composition ranges from 40 to 5,000 mPa.s.

4. The polyorganosiloxane composition as defined by claim 1, in solution in an organic solvent.

5. The polyorganosiloxane composition as defined by claim 1, in the form of an aqueous emulsion.

6. A substrate coated with the polyorganosiloxane composition as defined by claim 1.

7. The coated substrate as defined by claim 6, comprising from 0.1 to 10 g/m$^2$ of said polyorganosiloxane composition.

8. The coated substrate as defined by claim 6, comprising a coated flexible substrate.

9. The polyorganosiloxane composition as defined by claim 1, further comprising an inorganic filler material.

* * * * *